United States Patent [19]

Janick

[11] Plant 4,379

[45] Feb. 13, 1979

[54] HONEYSWEET PEAR TREE

[75] Inventor: Jules Janick, West Lafayette, Ind.

[73] Assignee: Purdue Research Foundation, West Lafayette, Ind.

[21] Appl. No.: 866,678

[22] Filed: Jan. 3, 1978

[51] Int. Cl.[2] ..... A01H 5/03

[52] U.S. Cl. ..... Plt./36

[58] Field of Search ..... Plt./36

*Primary Examiner*—Robert E. Bagwill

*Attorney, Agent, or Firm*—John R. Nesbitt

[57] ABSTRACT

This invention relates to a new, high quality pear with resistance to fireblight caused by *Erwinia amylovora* (Burr.) Winslow et al.

1 Drawing Figure

ORIGIN

A new and distinct pear seedling was derived from a selection made from seeds from a cross made in 1955 of "Seckel" × U.S. 220 (31S51) made in New Hampshire by Dr. L. F. Hough of Rutgers, The State University of New Jersey. The seeds (700 total) were received in September, 1955. From these a total of 137 seedlings were planted in the Purdue University Nursery in 1956 and screened for fireblight in 1957 by artificial innoculation. Fifty three seedlings showed little or no infection and were transplanted to the field in October, 1957. Severe winter injury decimated the fall planting and only eighteen seedlings survived. Of these, eight eventually fruited and one was selected. The selection was located in a cultivated tree at the Purdue University Orchard at the Throckmorton Farm, Lafayette, Ind., and assigned the progeny number PF 117-1 and known under its location designation as TH 7-230. This seedling first fruited in 1967 and was selected in 1969. The selection has since been topworked and tested in Lafayette, Ind.; Indianapolis, Ind.; Beltsville, Md.; and Harrow, Ontario, Canada. The topworked limbs have maintained the distinguishing characteristics of the clone.

GENERAL DESCRIPTION

The tree is spreading and does not defoliate even without spraying for leaf spotting diseases. The tree takes fireblight but strikes typically cork-off in 1 or 2 year old wood. The tree is considered to have at least "Kieffer" level of resistance.

The fruit can be picked the 2nd week in September in Lafayette, Ind. The pyriform-turbinate shaped fruit ranges from 2¼ - 2½ inches in diameter and 2½ to 2¾ inches in length, ripening to a golden russet. The flesh is very smooth and buttery with no detectable grit. The flavor is rich, very sweet, and resembles, 'Seckel'.

The new variety of pear is named 'Honeysweet'. 'Honeysweet' sets without pollinators but the size is reduced. Pollen is fertile.

'Honeysweet' is adapted to the Midwestern area of the U.S.

TECHNICAL DESCRIPTION

The following technical description follows Q. B. Zielinski's *Modern Systematic Pomology* and uses the color designations according to the Horticultural Chart used by the British Color Council in collaboration with the Royal Horicultural Society.

Form: pyriform to turbinate.
Color: ripens to Yellow Ochre 07/1.
Skin: fine russet overall.
Basin: shallow, broad, sloping.
Calyx: persistent closed, calyx tube funnel shaped (distinguishing characteristic), stamens marginal.
Core lines: clasping, distant.
Core: closed.
Flesh: buttery, sweet rich.
Quality: best.
Seeds: acute.
Use: local market.
Season: September 10 (Lafayette, Ind.).

I claim:

1. A new and distinct pear tree substantially as shown and described.

* * * * *

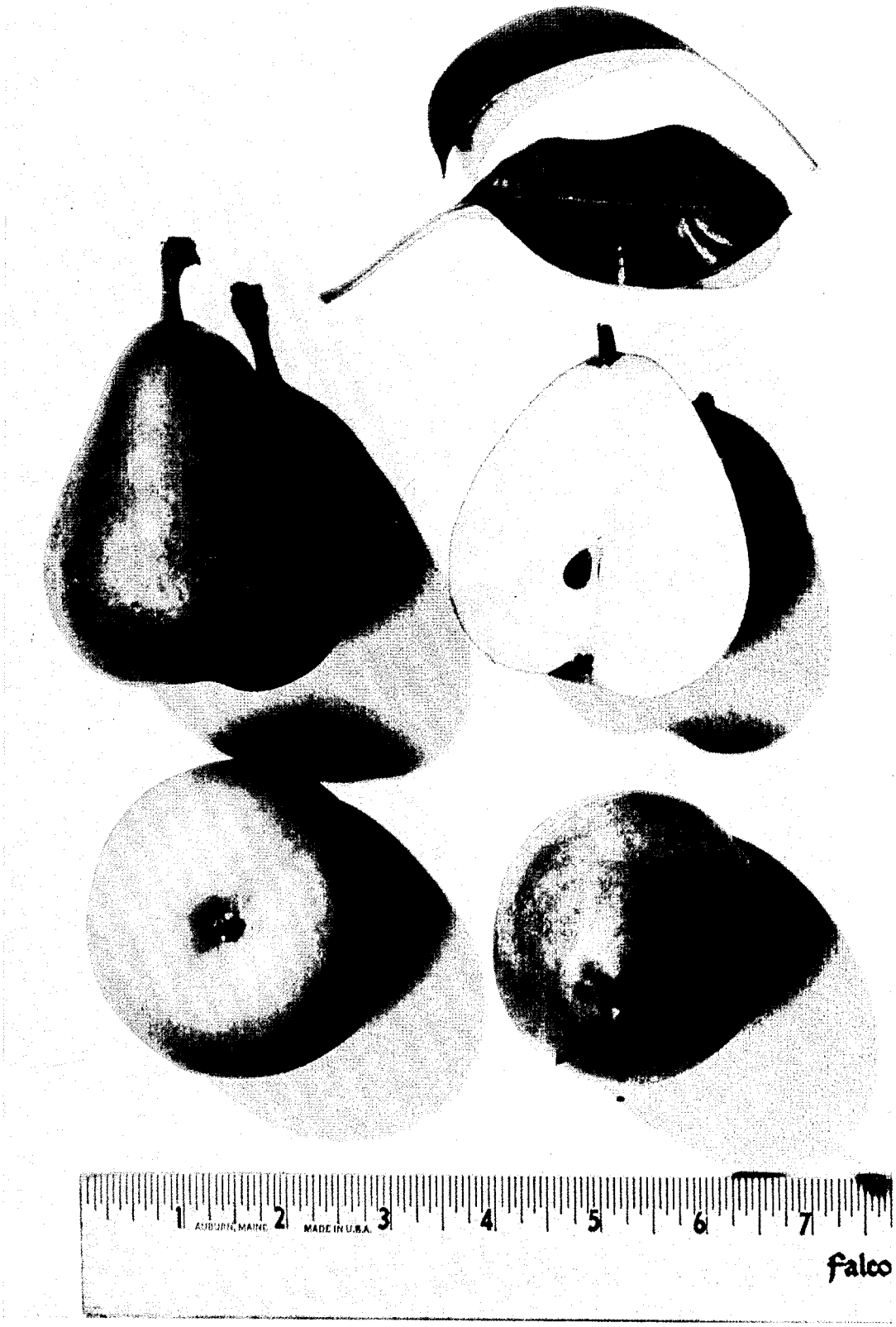
1
AUBURN, MAINE
2
MADE IN U.S.A.
3
4
5
6
7
falco